United States Patent
Kumar et al.

(10) Patent No.: US 7,022,511 B2
(45) Date of Patent: Apr. 4, 2006

(54) PROCESS FOR THE ISOLATION AND ACCLIMATIZATION OF BACTERIA FOR LIGNIN DEGRADATION

(75) Inventors: Rita Kumar, New Delhi (IN); Anil Kumar, New Delhi (IN)

(73) Assignee: Council of Scientific & Industrial Research, New Delhi (IN)

( * ) Notice: Subject to any disclaimer, the term of this patent is extended or adjusted under 35 U.S.C. 154(b) by 0 days.

(21) Appl. No.: 10/393,368

(22) Filed: Mar. 21, 2003

(65) Prior Publication Data

US 2004/0048355 A1    Mar. 11, 2004

Related U.S. Application Data

(60) Provisional application No. 60/365,809, filed on Mar. 21, 2002.

(51) Int. Cl.
- C12N 1/20 (2006.01)
- C12N 1/00 (2006.01)
- C12P 39/00 (2006.01)
- A61K 39/104 (2006.01)

(52) U.S. Cl. ............... 435/252.4; 435/253.6; 435/252.34; 435/253.3; 435/243; 435/410; 435/42; 424/269.1; 424/234.1

(58) Field of Classification Search ............. 424/269.1, 424/234.1; 435/42, 410, 243, 253.3, 252.34, 435/253.6, 252.4
See application file for complete search history.

(56) References Cited

OTHER PUBLICATIONS

Appl.Microbiology and Biotechnology, 2001. 57: 20-33.*
Biotechnology Letters, 1995, I 7: I 26 I—I 26.*
Biotechnology Letters, 2000. 22: 1 I 79-1 18 I.*
J. Environ Biol 2001 Jan; 22(1): 23-7.*
(Applied and Environmental Microbiology 1991 vol, 57, 3, 744-750).*
Hernandez et al 1994, Appl. Environ. Microbiol., Nov. 1994, 3909-3913, vol. 60, No. 11 Abstract Only.*
Frederick S. Archibald, "Lignin Peroxidase Activity Is Not Important in Biological Bleaching and Delignification of Unbleached Kraft Pulp by *Trametes versicolor*", Applied and Environmentl Microbiology, Sep. 1992, pp. 3101-3109, vol. 58-No. 9, American Society for Microbiology.

Brian P. Roy et al., "Effects of Kraft Pulp and Lignin on *Trametes versicolor* Carbon Metabolism", Applied and Environmental Microbiology, Jun. 1993, pp. 1855-1863, vol. 59-No. 6, American Society for Microbiology.

Jose Cardoso Duarte et al., "*Aspergilli* and lignocellulosics: Enzymology and biotechnological applications", FEMS Microbiology Reviews, 1994, pp. 377-386, vol. 13, Elsevier.

Maria Teresa Moreira et al., "Role of Organic Acids in the Manganese-Independent Biobleaching System of *Bjerkandera* sp. Strain BOS55", Applied and Environmental Microbiology, Jul. 1998, pp. 2409-2417, vol. 64-No. 7, American Society for Microbiology.

K. Haider et al., "Screening for Lignin Degrading Bacteria by Means of $^{14}$C-Labelled Lignins", Archives of Microbiology, Oct. 1978, pp. 103-106, vol. 119-No. 1, Springer International.

Ajit Varma et al., "Lignocellulose degradation by microorganisms from termite hills and termite guts: A survey on the present state of art", FEMS Microbiology Reviews, 1994, pp. 9-28, vol. 15, Elsevier.

M. M. Berrocal et al., "Solubilisation and mineralisation of [$^{14}$C]lignocellulose from wheat straw by *Streptomyces cyaneus* CECT 3335 during growth in solid-state fermentation", Appl. Microbiol. Biotechnol., 1997, pp. 379-384, vol. 48, Springer-Verlag.

Ian D. Reid, "Effects of Nitrogen Supplements on Degradation of Aspen Wood Lignin and Carbohydrate Components by *Phanerochaete chrysosporium*", Applied and Environmental Microbiology, Mar. 1983 pp. 830-837, vol. 45-No. 3.

O.K. Beg et al., "Microbial xylanases and their industrial applications: a review", Appl. Microbiol. Biotechnol., 2001, pp. 326-338, vol. 56, Springer-Verlag.

(Continued)

*Primary Examiner*—Lynette R. F. Smith
*Assistant Examiner*—Padma Baskar
(74) *Attorney, Agent, or Firm*—Foley & Lardner LLP

(57) ABSTRACT

The invention provides a novel process of lignin degradation using a consortium of bacteria. To date, biodegradation of lignin has been centered to fungi only. Degradation of lignin by bacteria confer a new understanding that may be of tremendous industrial significance. This invention also discloses the isolation and acclimatization of ligninolytic bacteria from a specific site.

6 Claims, No Drawings

OTHER PUBLICATIONS

J.H. Clarke et al., "A comparison of enzyme-aided bleaching of softwood paper pulp using combinations of xylanase, mannanase and α-galactosidase", Appl. Microbiol Biotechnol., 2000, pp. 661-667, vol. 53, Springer-Verlag.

N. Gupta et al., "A Thermostable Extracellular Xylanase from Alkalophilic *Bacillus* sp. NG-27", Biotechnology Letters, Nov. 1992, pp. 1045-1046, vol. 14-No. 11.

Michael J. Bailey et al., "Interlaboratory testing of methods for assay of xylanase activity", Journal of Biotechnology, 1992, pp. 257-270, vol. 23, Elsevier Science Publishers.

Toshiya Sasaki et al, "New Pulp Biobleaching System Involving Manganese Peroxidase Immobilized in a Silica Support with Controlled Pore Sizes", Applied and Environmental Microbiology, May 2001, pp. 2008-2212, vol. 67-No. 5, American Society for Microbiology.

Tamara Vares et al., "Secretion of Ligninolytic Enzymes and Mineralization of $^{14}$C-Ring-Labelled Synthetic Lignin by Three *Phlebia tremellosa* Strains", Applied and Environmental Microbiology, Feb. 1994, pp. 569-575, vol. 60-No. 2, American Society for Microbiology.

Ryuichiro Kondo et al., "Bleaching of Hardwood Kraft Pulp with Manganese Peroxidase Secreted from *Phanerochaete sordida* YK-624", Applied and Environmental Microbiology, Dec. 1994, pp. 4359-4363, vol. 60-No. 12, American Society for Microbiology.

J. Sealey et al., "Residual Lignin studies of laccase-delignified kraft pulps", Enzyme and Microbial Technology, 1998, pp. 422-426, vol. 23, Elsvier Science Inc.

* cited by examiner

PROCESS FOR THE ISOLATION AND ACCLIMATIZATION OF BACTERIA FOR LIGNIN DEGRADATION

This application claims Priority from Provisional Application 60/365,809 filed on Mar. 21, 2002.

FIELD OF THE INVENTION

Present invention relates to a novel, aerobic biological process for the degradation of lignin using the defined consortium of ligninolytic bacteria isolated from the specific site.

DESCRIPTION OF THE PRIOR ART

Fungi

Lignin is the most abundant aromatic polymer in the biosphere. It is found in the cell wall of all vascular plants in association with cellulose and hemicellulose. Because inter-unit bonds in lignin are not hydrolysable, lignin is difficult to degrade either chemically or biologically. Lignin surrounds cellulose in the plant cell wall forming a matrix, which is itself resistant to degradation. Lignin biodegradation is responsible for much of the natural destruction of wood in use, and it may have an important role in plant pathogenesis. On the other hand, potential applications utilizing lignin-degrading organisms and their enzymes have become attractive, because they may provide environmentally friendly technologies for the pulp and paper industry. To date, only a few groups of organisms are capable of degrading complex lignin polymers, and they are best exemplified by the white rot fungi. Most of the research concerning biodegradation of lignin has been centered on some fungi only such as *Phanerochaete chrysosporium, Streptomyces viridosporus, Pleurotus eryngii, Trametes trogii, Fusarium proliferatum* (Regaldo et al., 1997) etc. (1)

Wood-rotting basidiomycetous fungi that cause white rot in wood are the most efficient lignin degraders in nature (Kirk and Farrell, 1987; Eriksson et al., 1990), and they are perhaps nature's major agents for recycling the carbon of lignified tissues. No other microorganisms as pure culture have been described to mineralize lignified tissues as efficiently (Kirk and Cullen, 1998). They are a group of taxonomically heterogeneous higher fungi, characterized by their unique ability to depolymerize and mineralize lignin using a set of extracellular lignnolytic enzymes. Lignin degradation by white-rot fungi has been intensively studied during the last thirty years in relation to biotechnical applications such as biopulping, biobleaching, treating of pulp mill effluents, and soil bioremediation (Akhtar et al., 1992, 1998; Lamar et al., 1992; Messner and Srebotnik, 1994).

The enzymology and molecular biology of lignin degradation has been mainly studied in *Phanerochaete chrysosporium* (Gold and Alic, 1993; Cullen, 1997; Kirk and Cullen, 1998). Many of the enzymes necessary for lignin degradation were not characterized before the beginning of the 1980s when virtually only laccase had been known. Since the discovery of two important peroxidases in the beginning of the 1980s, namely lignin peroxidases (LiPs) in 1983 and manganese peroxidases (MnPs) in 1984 (Kirk and Farrell, 1987), an array of enzymes have been isolated from fungi and characterized in detail.

LiP (lignin peroxidase) is believed to be one of the key enzymes in lignin biodegradation by white rot fungi. DNA probes specific for the genes encoding major lignin peroxidases (LiP) isozymes of *P. chrysosporium* were constructed. These probes were used to study the temporal expression of LiP enzymes in defined low nitrogen medium. (Boominathan et al. 1993).

*Aspergilli*, the versatile ascomycetes are also found to transform at a rapid rate a wide spectrum of lignin related aromatic compounds. They are shown to overproduce high levels of hemicellulolytic enzymes. (4)

Maria Teresa et al. have shown that *Bjerkandera* sp. Strain BOS55 is a white rot fungus that can bleach EDTA extracted eucalyptus oxygen delignified Kraft pulp (UKP) without any requirement for manganese. Furthermore, under manganese free conditions, addition of simple physiological organic acids (e.g. Glycolate, glyoxylate, oxalate and others) at 1–5 mM stimulated brightness gains and pulp delignification two to three fold compared to results not receiving acids. The stimulation was attributed to increase production of MnP and LiP as well as increased physiological concentrations of veratryl alcohol and oxalate. These factors contributed to greatly improved production of superoxide anion radicals, which may have been accounted for the more extensive biobleaching. (5)

Till now, all the basics and applied research work has centered on fungi only. In case of biobleaching of raw pulp, the application of fungi is not feasible due to its structural hindrance caused by fungal filaments. Therefore, identification of bacteria having lignin oxidizing enzymes would be of significant importance.

Bacteria

The role of bacteria in lignin biodegradation is still a matter of conjecture. Some workers have demonstrated that either mixed (Sundman et al., 1968) or pure culture of bacteria (Sorensen, 1962) can grow on lignin as a carbon source. *Pseudomonas* spp. was claimed by Kawakami (1976) and Odier and Monties (1977) to degrade plant lignins. Odier and Montis also indicated several other bacterial strains that can use within seven days time more than 50% of the lignin supplied in a mineral medium containing glucose.

Several *Nocardia* and *Pseudomonas* spp. as well as some unidentified bacteria, isolated from lake water containing high loads of waste lignin, were tested for their capacity to release $^{14}CO_2$ from specifically $^{14}C$-labelled dehydropolymer of coniferyl alcohol (DHP) or corn stack lignins. However only some of them could release significant amounts of $^{14}CO_2$ from the labeled lignin. The tested *Nocardia* spp. was more active than the *Pseudomonas* spp. and the unidentified bacteria.(6)

Actinomycetes are filamentous bacteria which are found in soil and composts where lignocellulose is decomposed. Several reports provide evidence that several species belonging to the genus *Streptomyces* are able to degrade lignin. Other lignin degrading Actinomycetes include *Thermomonospora mesophila, Actinomadura, Micromonospora* with *Streptomyces* exibiting the highest lignin degrading ability. In most of the studies, the lignin degrading enzyme was produced at higher levels in cultures containing lignocellulose which suggests that an induction mechanism was active.

Ajit Verma et al.(1994) while working on symbiotic relationship between termites and their intestinal microbes concluded that both termite soil and termite gut bacteria play an important role in polymer depolymerization. Gut bacteria have the capacity to degrade cellulosic and hemicellulosic materials more efficiently. Several bacterial isolates which hydrolyze cellulose and hemicellulose have been obtained in pure culture from the termite gut. Some of these are *Arthrobacter* sp., *Bacillus cereus, Clostridium* sp., *Micrococcus* sp., *Streptomyces* sp., *Serratia marcescens*. Only a few xylan decomposing bacteria have been obtained from the termite gut (*Micrococcus luteuns, Pseudomonas aeruginosa*). The question of lignin degradation by termites is intriguing, since much of the termite gut is anaerobic and natural anaerobic mechanisms of lignin degradation are unknown. (7)

Berrocal et al. (1997) have shown that cell free filtrates from *streptomyces sp.* Grown in solid state fermentation were capable of solubilising up to 20% of the [$^{14}$C] lignin. The activity of two enzymes, extracellular peroxidase and phenol oxidase (laccase) was found to correlate with both solubilisation and mineralisation rates of lignin.(8)

The presence of bacteria in rotted wood often in association with fungi has been the subject of numerous reports. However, their exact role in degradation of wood components is still unclear. While the availability of nutrient nitrogen represses metabolism of synthetic $^{14}$C lignin to $CO_2$ by *Phanerochaete Chrysosporium*, high levels of organic nitrogen were optimal for lignin degradation by the bacterium *Streptomyces badius*. (9)

Few bacterial isolates which exhibited a remarkable capability of bleaching the hardwood kraft pulp as reported in a previous pending patent application, have shown lignin degradation capability.

Enzymes are the catalytic cornerstones of metabolism, and as such are the focus of intense worldwide research, not only in biological community, but also with process designers/engineers, chemical engineers, and researchers working in other scientific fields. Since ancient times, enzymes have played a central role in many manufacturing process, such as in the production of wine, cheese, bread etc. The latter half of the twentieth century saw an unprecedent expansion in our knowledge of the use of microorganisms, their metabolic products, and enzymes in a broad area of basic research and their potential industrial applications. Only in the past two decades, however have microbial enzymes been used commercially in the Pulp and Paper industry. (10)

The most common application of enzymes in paper industry is to enhance bleaching. At least 15 patents or patent disclosures dealing with enzymatic treatments to enhance bleaching of Kraft pulps were submitted between 1988 and 1993.

Lignin, correctly known as "nature's plastic", although resistant to microbial attack, certain filamentous fungi is capable of degrading it to the level of $CO_2$. Until 1981, it was not even known whether enzymes are involved in lignin depolymerization. Ming Tien et al. from university of Michigan have discovered enzymes that degrade lignin.

The major enzymes involved in lignin biodegradation by fungi are two extracellular heme containing peroxidases: Lignin Peroxidase (LiP, EC 1.11.1.14) and Manganese Peroxidases (MnP, EC: 1.11.1.13) (Kirk et al., 1987), Gold et al. (1989); Hatakka (1994). The main difference between LiP and MnP is the nature of substrate that is oxidized. LiP is capable of oxidizing non phenolic or phenolic lignin structures directly to yield aryl cation radicals and phenoxy radicals, respectively. (Kirk, 1987). For MnP, the primary reducing substrate is divalent manganese ion $Mn^{2+}$. The catalytic cycle of MnP in the presence of appropriate chelators generates highly reactive $Mn^{3+}$ chelate complexes that are able to oxidize various phenols and carbon centered radicals. (Wariishi et al., 1989; Hofrichter et al., 1998).

Usually MnP is not able to oxidize or depolymerize the more recalcitrant non-phenolic lignin structures that make up about 90% of the lignin in wood. Interestingly, it seems that primary attack on lignin requires low molecular weight agents, because LiP and other enzymes are too large to penetrate lignocellulose. (Call et al., 1997). Because of these discrepancies, it has been proposed that there are mechanisms that enable MnP to cleave non-phenolic lignin structures via the action of small mediators such as thiyl or lipid radicals. (Wariishi et al., (1989), Bao et al., (1994)).

The Mn (II) concentration of the growth medium strongly affects the secretion patterns of lignin peroxidase and laccase. Mn Peroxidase was not found in fast protein liquid chromatography profiles of extracellular proteins under either low (2.4 µM) or elevated (24 and 120 µM) Mn (II) concentrations.(16)

The role of one more enzyme, extracellular phenol oxidases (laccases) in lignin degradation has been suggested and it has recently been demonstrated that laccase can take part in lignin degradation. (Bourbonnais and Paice 1990; 1992: Srinivasan et al. 1995). Laccase is a type of copper containing polyphenol oxidase known to catalyze the oxidation of a range of inorganic and aromatic substances by the removal of electrons with the concomitant reduction of $O_2$ to water. But its application in Bioblecahing has to be proved yet.

CITED REFERENCES (1) Etienne Odier and Isabelle Artaud 'Degradation of Lignin'. Prof. Dr. Annele Hatakka, 'Biodegradation of Lignin'.
(2) Frederick S. Archibald, 'Lignin Peroxidase activity is not important in biological bleaching and delignification of unbleached kraft pulp by Trametes versicolor' *Appl. and Env. Microbiol.*, September 1992 p. 3101–3109.
(3) Brian P. Roy and Frederick Archibald, 'Effects of Kraft pulp and lignin on Trametes versicolor carbon metabolism', *Appl. and Environmental Microbiol.*, June 1993, P. 1855–1863.
(4) Daurte J C, Costa-Ferreira M; '*Aspergilli* and Lignocellulosics: Enzymology and biotechnological applications', *FEMS Microbiol. Rev., March* 1994; 13 (2–3):377–86.
(5) Maria Teresa, Gumersindo Feijoo, tuned mester, Pablo Mayorga, Reyes sierra-Alvarez and Jim A. Field.; 'Role of Organic acids in the Manganese independent biobleaching system of *Bjerkandera sp.* Strain BOS55', *Appl. and Env. Microbiol.*, July 1998, p. 2409–2417.
(6) K. Haider, J, Trojanowski, and V. Sundman, 'Screening for lignin degrading Bacteria by means of [$^{14}$C] labeled lignin' *Arch. Microbiol.* 119, 103–106 (1978).
(7) Varma A., Koll's B. K., Paul J., Saxena S., Koniig H; Lignocellulose degradation by microorganisms from termite hills and termite guts: A survey on the present state of art. *FEMS Microbiology Reviews* 15 (1994) 9–28.
(8) M. M. Berrocal. J. Rodriguez. A. S. Ball, M. I. Perez-Lebric. M. E. Alias. 'Solubilization and mineralization of [$^{14}$C] lignocellulose from wheat straw by *Streptomyces cyaneus* CECT 3335 during growth in solid state fermentation', *Appl. Microbiol. Biotechnol* (1997) 48:379–384.
(9) Ian D. Reid, 'Effects of Nitrogen supplements on degradation of aspen wood lignin and carbohydrate components by *P. chrysosporium*', *Appl. And Env. Micro,* March 1983, p. 830–837.
(10) Q. K. Beg. M. Kapoor. L. Mahajan. G. S. Hoondal, Microbial xylanases and their industrial applications, A Review', *Appl. Microbiol. Biotech.* (2001) 56:326–328.

(11) J. H. Clarke, K. Davidson, J. E. Rixon, J. R. Halstead, M. P. Fransen. H. J. Gilbert, G. P. Hazlewood., 'A comparison of enzyme aided bleaching of softwood paper pulp using combinations of xylanase, mannanase and 2-galactosidase.' *Appl. Microbiol. Biotechnol.* (2000) 53: 661–667.

(12) Thomas W. Jeffries, 'Enzymatic treatments of pulps: Opportunities for the Enzyme Industry in Pulp and Paper Manufacture'.

(13) N. Gupta, R. M. Vohra and G. S. Hoondal. 'A thermophillic extracellular xylanase from alkalophilic *Bacillus sp.* NG-27', *Biotechnology Letters,* vol. 14 No. 11 (November 1992) pp. 1045–1046.

(14) Michael J. Bailey, Peter Biely and Kaisa Poutanen, 'Interlaboratory testing of methods for assay of xylanase activity', Journal of Biotechnology, 23 (1992) 257–270.

(15) Toshiya susaki, Tsutomu Kajono, BoLi, Hidehiko Sugiyama, and Harua Takatashi; 'New pulp biobleaching system involving manganese peroxidase immobilized in a silicon support with controlled pore sizes', Appl. and Env. Microbiol. May 2001, p 2208–2212.

(16) Tamara Vares, Outi Niemenmaa and Annele Hatakka, 'Secretion of Lignolytic enzymes and mineralization of $^{14}$C-ring labeled synthetic lignin by three Phlebia tremellosa strains', Appl. and Environmental Microbiol. February 1994 569–573.

(17) Ryuichiro Kondo, Koichi Harazono, and Kokki Sakai; 'Bleaching of hardwood Kraft pulp with Manganese Peroxidase secreted from Phanerochaete sordida YK-624'. *Appl. and Env. Microbiol.* December 1994, p. 4359–4363.

(18) J. C. Rols, G. Goma, C. Fonade. 'Biotechnology and the paper industry, Aerated lagoon for the wastewater treatment'.

(19) J. Sealey and A. J. Ragauskas, 'Residual lignin studies of laccase-delignified Kraft pulps', *Enz. And Micro Tech.* 23: 422–426, 1998.

Objects of the Invention

The main object of the present invention is to provide a novel consortium of ligninolytic bacteria for degradation of lignin.

Another object of the present invention is to provide a novel biological process for the degradation of lignin using the above-defined consortium of ligninolytic bacteria.

Yet another object of the invention is to provide a process for preparing a consortium of ligninolytic bacteria capable of degrading lignin.

SUMMARY OF THE INVENTION

The present invention provides a novel consortium of ligninolytic bacteria for degradation of lignin and also a biological process for the degradation of lignin using said consortium of ligninolytic bacteria. Ligninolytic bacteria were isolated from a specific Indian site where sawdust continually accumulated over the long period. The said bacteria were acclimatized to improve their capability to degrade lignin and finally formulated in a consortium to degrade the lignin.

DETAILED DESCRIPTION OF THE INVENTION

The present invention relates to a synergistic consortium of ligninolytic bacteria for degradation of lignin, said consortium comprising bacterial strains CBTCC/52-03, CBTCC/53-03 and CBTCC54-03 deposited on Mar. 5, 2003 at the International Depository at Microbial Type Culture Collection & Gene Bank (MTCC) Institute of Microbial Technology (IMTECH), Sector 39-A Chandigarh, 160 036 (Union Territory) India, and having accession numbers MTCC 5094, MTCC 5095 and MTCC 5098 respectively in any possible combination. MTCC 5094, MTCC 5095 and MTCC 5098 respectively correspond to *Serratia marcescens. Pseuodomonas aeruginosa* and *Pseuodomonas aeruginosa.*

In an embodiment of the present invention, the consortium comprises bacterial strains MTCC 5094, MTCC 5095 and MTCC 5098.

In another embodiment of the present invention, the consortium comprises bacterial strains MTCC 5094, MTCC 5095 and MTCC 5098 in the range of 20 to 40% by wt. each.

In yet another embodiment of the present invention, the consortium comprises bacterial strains MTCC 5094, MTCC 5095 and MTCC 5098 are in equal proportions.

In still another embodiment of the present invention, wherein the bacteria are isolated from a mixture of sawdust and soil.

In one more embodiment of the present invention, the bacteria are isolated from a mixture of sawdust and soil from Roorkhee, India.

In one another embodiment of the present invention, the consortium exhibits lignin degradation of up to 0.8%.

In a further embodiment of the present invention, the characteristics of MTCC 5094 are as follows: Gram—Negative, Shape—Small rods.

In an embodiment of the present invention, the characteristics of MTCC 5095 are as follows: Gram—Negative, Shape—Cocci.

In another embodiment of the present invention, the characteristics of MTCC 5098 are as follows: Gram—Negative, Shape—Long rods.

The bacterial isolates concerned with the present invention are being deposited at Institute of Genomics and Integrative Biology (IGIB) as CBTCC, and their identification is underway.

| S. No. | Culture | Accession No. |
|---|---|---|
| 1. | CBTCC/52-03 | MTCC 5094 |
| 2. | CBTCC/53-03 | MTCC 5095 |
| 3. | CBTCC/54-03 | MTCC 5098 |

These bacterial isolates are exhibiting a remarkable capability to degrade the lignin under defined conditions.

The bacterial isolates in the present invention have been isolated from a wood workshop situated at Roorkee, India, where sawdust continually accumulated over the period of 10–12 years.

The invention further provides a process of isolation and acclimatization of bacterial isolates capable to degrade the lignin which comprises:

a) enriching the bacterial flora of the said site using soil extract and particular inducers under defined conditions;

b) using different media (0.3 lignin+agar; soil extract+agar; 50% soil extract+agar; 0.3% lignin+50% soil extract) to entrap the maximum bacterial flora from the said site;

c) culturing the said bacteria isolated from specific site under defined conditions such as media, temperature, pH, carbon source etc.;

d) checking the lignin degrading capability of isolated bacterial isolates by inoculating them in 10 ml 0.4% lignin;
e) lignin degradation was estimated by a known spectrophotometric method;
f) selecting the bacterial isolates which can decolorize the lignin effectively;
g) acclimatizing the short listed bacterial isolates for higher concentration of lignin to see the enhancement of their ligninolytic activity;
h) Further short listing and formulation of different bacterial isolates in order to see their synergistic effect for lignin degradation;
i) culturing the said bacteria under defined conditions for the detection of enzyme activity in crude as well as in concentrated sample. MSM having 1.0% glucose was used to grow the culture in 2 litre flask having 1000 ml culture. The culture flask was incubated at 30° C./120 rpm for 3 days in order to obtain heavy growth;
j) centrifuging the resulting culture after attaining the heavy growth O.D. (1.00);
k) collecting the supernatent and concentrating through ammonium sulphate precipitation followed by dialysis;
l) assaying the lignin peroxidase in both the samples, crude as well as in concentrated by measuring the product (veratryldehyde)formation spectrophotometrically at 310 nm.

In an embodiment of the present invention, the bacteria are isolated from specific sawdust site located in Roorkee, India.

In another embodiment of the present invention, enrichment of the soil from said site is done by taking 5 g of fresh soil in the 500 ml autoclaved flask containing 100 ml soil extract, 0.3% lignin, 1 mM veratryl alcohol and 50 ul Candid B. Enrichment flask is kept at 120 rpm for 96 hours at 30° C.

In another embodiment of the present invention, four types of different media (0.3 lignin+agar; soil extract+agar; 50% soil extract+agar; 0.3% lignin+50% soil extract) are used to entrap the maximum bacterial flora of the said site.

In another embodiment of the present invention, isolated bacterial isolates are cultured under defined conditions such as media, temperature, pH, carbon source etc.

In another embodiment of the present invention, all the bacterial isolates are tested for their lignin degrading capability by inoculating them in 10 ml 0.4% lignin. Lignin degradation was estimated by a known spectrophotometric method.

In another embodiment of the present invention, some selected bacterial isolates are acclimatized for higher concentration of lignin to see the enhancement of their ligninolytic activity. Bacteria are inoculated in lignin ranging from 0.5% to 1.0% and kept at 30° C. for a period of three months. Lignin degradation was estimated by a known spectrophotometric method.

In another embodiment of the present invention, further short listed bacterial isolates are formulated in a number of consortia to see their synergistic effect for lignin degradation.

In another embodiment of the present invention, MSM having 1.0% glucose is used to grow the culture in 2 litre flask having 1000 ml culture for the enzyme study. The culture flasks are incubated at 30° C./120 rpm for 3 days in order to obtain heavy growth.

In another embodiment of the present invention, cultures are centrifuged and supernatent is collected followed by 80% ammonium sulphate precipitation and dialysis.

In another embodiment of the present invention, lignin peroxidase is assayed in both the samples, crude as well as in concentrated by measuring the product (veratryldehyde) formation spectrophotometrically at 310 nm.

The present invention further provides a process of lignin degradation, said process comprising inoculating the bacterial consortium comprising bacterial strains CBTCC/52-03, CBTCC/53-03 and CBTCC54-03 deposited at International Depository at IMTECH, Chandigarh, India, and having accession numbers MTCC 5094, MTCC 5095 and MTCC 5098 in an solution containing lignin for 1 to 5 days at temperature between 25 to 35° C.

In an embodiment of the present invention, the bacterial consortium comprises whole cell bacterial isolates of bacterial strains MTCC 5094, MTCC 5095 and MTCC 5098.

In another embodiment of the present invention, the consortium comprises bacterial strains MTCC 5094, MTCC 5095 and MTCC 5098.

In yet another embodiment of the present invention, the consortium comprises bacterial strains MTCC 5094, MTCC 5095 and MTCC 5098 in the range of 20 to 40% by wt. each.

In still another embodiment of the present invention, the consortium comprises bacterial strains MTCC 5094, MTCC 5095 and MTCC 5098 in equal proportions.

In one more embodiment of the present invention, the bacteria are isolated from a mixture of sawdust and soil.

In one another embodiment of the present invention, the bacteria are isolated from a mixture of sawdust and soil from Roorkhee, Uttar Pradesh, India.

In a further embodiment of the present invention, the consortium exhibits lignin degradation of up to 0.8%.

For the isolation of ligninolytic bacteria, proper enrichment was done. To improve the yield of desired bacteria, 5 g of fresh soil from the said site was inoculated in the 500 ml autoclaved flask containing 100 ml soil extract, 0.3% lignin and 50 ul Candid B (antifungal). Enrichment flask was kept at 120 rpm for 96 hours at 30° C.

For the preparation of soil extract, 1 Kg soil was taken and dried at 50° C. for 2 hours. 400 g of dried soil was dissolved in 960 ml single distilled water and autoclaved at 15 lbs for 1 hour. After autoclaving, the sample was centrifuged at 5000 rpm for 10 minutes. The supernatant (extract) was collected and stored in sterile bottle for the preparation of enrichment flask till further use.

The enriched soil samples were serially diluted in 0.85% saline. 100 ul from each respective dilution was spread onto petriplates containing soil extract, 50% nutrient agar and 0.2% lignin for the the isolation of ligninolytic bacteria. The plates thus obtained were incubated at 30±2° C. for 24–96 hrs in inverted position.

On the basis of colony morphology and colour, total 36 isolates were selected to check their ligninolytic activity. The single isolated colonies were picked and streaked on fresh plates containing the same medium. The above step was repeated till pure colonies were obtained.

To check the ligninolytic activity of the isolated bacteria, 10 ml of 0.4% lignin was taken in 30 ml test tubes and all the bacterial isolates were inoculated individually. After 3 days, different bcaterial isolates showed different degree of decolorization of lignin. Lignin degradation was estimated by a known spectrophotometric method.

On the basis of lignin decolorization, total 15 bacterial isolates out of 36 isolates were selected for further study. To enhance the ligninolytic activity of the selected bacterial isolates, acclimatization was done for higher concentration of lignin. All the 15 isolates were inoculated in 10 ml lignin for the range from 0.5% to 1.00%. All the tubes were kept at 30° C. for three months. After the long acclimatization, 8 bacterial isolates were chosen for the further study. The selected isolates were able to decolorize the lignin upto 0.7%. Lignin degradation was estimated by a known spectrophotometric method.

In order to see the synergistic effect of these bacterial isolates, a number of consortia were designed and tested for their capability of degrading the lignin. One consortium comprising of three bacteria designated as MTCC 5094, MTCC 5095 and MTCC 5098 was found able to degrade the lignin upto 0.8%.

To find out the mechanism of lignin degradation at enzyme level, enzyme assay for lignin peroxiadse, a key enzyme for lignin degradation, was carried out. All the three bacteria were inoculated in 1 litre minimal salt medium (MSM) having 1% glucose. For the induction of ligninolytic enzymes, 1 mM veratryl alcohol was added to the cultures. All the cultures were incubated at 30–35° C. for three days under shaking conditions (100–120 rpm). After observing the heavy bacterial growth, all the cultures were centrifuged at 10,000 rpm at 4° C. Supernatent was collected to check the enzyme activity.

For the concentration of extracellular enzymes, 80% ammonium sulphate precipitation was carried out using 100% saturated ammonium sulphate solution followed by subsequent dialysis.

Enzyme assay for lignin peroxidase was performed for both, crude cell free extract as well as concentrated sample. For the enzyme assay, 10 mM veratryl alcohol, 5 mM $H_2O_2$ and 400 µl enzyme solution was added in tartaric acid (pH 3) buffer. The formation of product (veratryldehyde) was monitored at 310 nm. Lignin peroxidase catalyzes the oxidation of veratryl alcohol by $H_2O_2$ to veratryldehyde. Veratry alcohol exhibits no absorbance at 310 nm whereas veratrlydehyde absorbs strongly (molar extinction coefficient=9300 M−1 cm−1). All the three bacterial isolates showed different degree of ligninolytic activity.

The present invention is further described with reference to the accompanying examples, which are given by way of illustration and hence, should not be construed to limit the scope of the present invention in any manner.

EXAMPLE 1

In the endeavor of exploring ligninolytic bacteria, strategic isolation was done to entrap the maximum ligninolytic bacterial flora from the specific site.

Isolation point was a workshop situated at Roorkee, India, where sawdust continually accumulated over the period of 10–12 years.

For the isolation of ligninolytic bacteria, proper enrichment was done. To improve the yield of desired bacteria, 5 g of fresh soil from the said site was inoculated in the 500 ml autoclaved flask containing 100 ml soil extract, 0.3% lignin and 50 ul Candid B. Enrichment flask was kept at 120 rpm for 96 hours at 300 C.

For the preparation of soil extract, 1 Kg soil was taken and dried at 500 C. for 2 hours. 400 g of dried soil was dissolved in 960 ml single distilled water and autoclaved at 15 lbs for 1 hour. After autoclaving, the sample was centrifuged at 5000 rpm for 10 minutes. The supernatant (extract) was collected and stored in sterile bottle for the preparation of enrichment flask and further use.

The enriched soil samples were serially diluted in 0.85% saline. 100 ul from each respective dilution was spread onto petriplates containing soil extract, 50% nutrient agar and 0.2% lignin for the isolation of ligninolytic bacteria. The plates thus obtained were incubated at 30±2° C. for 24–96 hrs in inverted position.

On the basis of colony morphology and color, total 36 isolates were selected to check their ligninolytic activity. The single isolated colonies were picked and streaked on fresh plates containing the same medium. The above step was repeated till pure colonies were obtained.

EXAMPLE 2

For the isolation of ligninolytic bacteria, proper enrichment was done. To improve the yield of desired bacteria, 5 g of fresh soil from the said site was inoculated in the 500 ml autoclaved flask containing 100 ml soil extract, 0.3% lignin and 50 ul Candid B. Enrichment flask was kept at 120 rpm for 96 hours at 300 C.

For the preparation of soil extract, 1 Kg soil was taken and dried at 500 C for 2 hours. 400 g of dried soil was dissolved in 960 ml single distilled water and autoclaved at 15 lbs for 1 hour. After autoclaving, the sample was centrifuged at 5000 rpm for 10 minutes. The supernatant (extract) was collected and stored in sterile bottle for the preparation of enrichment flask and further use.

The enriched soil samples were serially diluted in 0.85% saline. 100 ul from each respective dilution was spread onto petriplates containing soil extract, 50% nutrient agar and 0.2% lignin for the isolation of ligninolytic bacteria. The plates thus obtained were incubated at 30±2° C. for 24–96 hrs in inverted position.

On the basis of colony morphology and color, total 36 isolates were selected to check their ligninolytic activity. The single isolated colonies were picked and streaked on fresh plates containing the same medium. The above step was repeated till pure colonies were obtained.

To check the ligninolytic activity of the isolated bacteria, 10 ml of 0.4% lignin was taken in 30 ml test tubes and all the bacterial isolates were inoculated individually. After 3 days, different bacterial isolates showed different degree of decolorization of lignin. Lignin degradation was estimated by a known spectrophotometric method.

TABLE 1

| Bacterial degradation of lignin (0.4%) as a sole carbon source | | |
|---|---|---|
| Isolate No. | Lignin percentage | Decolourization |
| L1 | 0.4% | 5% |
| L2 | 0.4% | 10% |
| L3 | 0.4% | 4% |
| L4 | 0.4% | 29% |
| L5 | 0.4% | 36% |
| L6 | 0.4% | 9% |
| L7 | 0.4% | 4% |
| L8 | 0.4% | 31% |
| L9 | 0.4% | 20% |
| L10 | 0.4% | 35% |
| L11 | 0.4% | 40% |
| L12 | 0.4% | 5% |
| L13 | 0.4% | 32% |
| L14 | 0.4% | 14% |
| L15 | 0.4% | 12% |
| L16 | 0.4% | 5% |
| L17 | 0.4% | 6% |
| L18 | 0.4% | 23% |
| L19 | 0.4% | 9% |
| L20 | 0.4% | 38% |
| L21 | 0.4% | 12% |
| L22 | 0.4% | 30% |

TABLE 1-continued

Bacterial degradation of lignin (0.4%) as a sole carbon source

| Isolate No. | Lignin percentage | Decolourization |
|---|---|---|
| L23 | 0.4% | 25% |
| L24 | 0.4% | 6% |
| L25 | 0.4% | 14% |
| L26 | 0.4% | 4% |
| L27 | 0.4% | 42% |
| L28 | 0.4% | 29% |
| L29 | 0.4% | 33% |
| L30 | 0.4% | 11% |
| L31 | 0.4% | 13% |
| L32 | 0.4% | 15% |
| L33 | 0.4% | 7% |
| L34 | 0.4% | 11% |
| L35 | 0.4% | 34% |
| L36 | 0.4% | 36% |

EXAMPLE 3

For the isolation of ligninolytic bacteria from specific site, proper enrichment was done. To improve the yield of desired bacteria, 5 g of fresh soil from the said site was inoculated in the 500 ml autoclaved flask containing 100 ml soil extract, 0.3% lignin and 50 ul Candid B. Enrichment flask was kept at 120 rpm for 96 hours at 300 C.

For the preparation of soil extract, 1 Kg soil was taken and dried at 500 C for 2 hours. 400 g of dried soil was dissolved in 960 ml single distilled water and autoclaved at 15 lbs for 1 hour. After autoclaving, the sample was centrifuged at 5000 rpm for 10 minutes. The supernatant (extract) was collected and stored in sterile bottle for the preparation of enrichment flask and further use.

The enriched soil samples were serially diluted in 0.85% saline. 100 ul from each respective dilution was spread onto petriplates containing soil extract, 50% nutrient agar and 0.2% lignin for the isolation of ligninolytic bacteria. The plates thus obtained were incubated at 30±2° C. for 24–96 hrs in inverted position.

On the basis of colony morphology and color, total 36 isolates were selected to check their ligninolytic activity. The single isolated colonies were picked and streaked on fresh plates containing the same medium. The above step was repeated till pure colonies were obtained.

To check the ligninolytic activity of the isolated bacteria, 10 ml of 0.4% lignin was taken in 30 ml test tubes and all the bacterial isolates were inoculated individually. After 3 days, different bacterial isolates showed different degree of decolorization of lignin.

On the basis of lignin decolorization, total 15 bacterial isolates, namely, L4, L5, L8, L10, L11, L13, L18, L20, L20, L22, L23, L27, L28, L29, L35 AND L36 from 36 were selected for further study. To enhance the ligninolytic activity of the selected bacterial isolates, acclimation was done for higher concentration of lignin. All the 15 isolates were inoculated in 10 ml lignin for the range from 0.5% to 1.00%. All the tubes were kept at 30° C. for three months. After the long acclimatization, 8 bacterial isolates, namely, L4, L5, L10, L13, L28, L29, L35 and L36 were chosen for the further study. Lignin degradation was estimated by a known spectrophotometric method the selected isolates had been able to decolorize the lignin upto 0.7%. (Table 2)

TABLE 2

Acclimatization of selected ligninolytic bacteria to higher concentration of lignin

| Isolate No. | 0.5% | 0.6% | 0.7% | 0.8% | 0.9% | 1.0% |
|---|---|---|---|---|---|---|
| L4  | 30% | 25% | 11% | 0.0% | 0.0% | 0.0% |
| L5  | 40% | 30% | 12% | 1.0% | 0.0% | 0.0% |
| L8  | 34% | 22% | 10% | 0.0% | 0.0% | 0.0% |
| L10 | 33% | 27% | 12% | 0.0% | 0.0% | 0.0% |
| L11 | 37% | 27% | 10% | 0.0% | 0.0% | 0.0% |
| L13 | 30% | 23% | 14% | 1.0% | 0.0% | 0.0% |
| L18 | 20% | 15% | 8%  | 0.0% | 0.0% | 0.0% |
| L20 | 33% | 20% | 7%  | 0.0% | 0.0% | 0.0% |
| L22 | 25% | 15% | 3%  | 0.0% | 0.0% | 0.0% |
| L23 | 24% | 14% | 2%  | 0.0% | 0.0% | 0.0% |
| L27 | 40% | 19% | 11% | 0.0% | 0.0% | 0.0% |
| L28 | 26% | 20% | 15% | 2.0% | 0.0% | 0.0% |
| L29 | 35% | 30% | 12% | 0.0% | 0.0% | 0.0% |
| L35 | 40% | 30% | 20% | 3.0% | 0.0% | 0.0% |
| L36 | 39% | 22% | 14% | 1%   | 0.0% | 0.0% |

EXAMPLE 4

In order to see the synergistic effect of the acclimatized bacteria, a number of consortia were designed and tested for their capability of degrading the lignin. Consortia were designed in taking three bacterial isolates together. All the consortia were made from 8 bacterial isolates, namely, L4, L5, L10, L13, L28, L29, L35 and L36, which have been able to degrade the lignin upto 0.7%. These consortia were tested for their ligninolytic activity in a synergistic manner.

To make the inoculum from consortium for biodegradation study, a loop from agar plate of three different bacteria were inoculated individually in 10 ml MSM with 1% glucose. The cultures were incubated at 30° C. for 16–24 hours in an incubator shaker at 100–120 rpm. After incubation, optical density was measured at 650 nm. Optical density of the culture was maintained to 1.00 either by diluting or concentrating the bacterial suspension. All the three cultures were mixed together in equal proportion in order to make the inoculum. Different concentrations of lignin (0.7%, 0.8%, 0.9%, 1.0%) were inoculated by the inoculum of different consortia. All the tubes were incubated for 3 days at 30° C. Lignin degradation was estimated by a known spectrophotometric method. Finally a consortium comprising the bacterial isolate, L35, L36 and L13, was selected as a potent lignin degrader which was able to degrade the lignin upto 0.8%

TABLE 3

Synergistic effect of ligninolytic bacteria on lignin degradation.

| Consortia No. | 0.7% | 0.8% | 0.9% | 1.0% |
|---|---|---|---|---|
| 1 | 13% | 6.0%  | 0.0% | 0.0% |
| 2 | 12% | 5.0%  | 0.0% | 0.0% |
| 3 | 18% | 12.0% | 2.0% | 0.0% |
| 4 | 12% | 11.0% | 0.0% | 0.0% |
| 5 | 14% | 10.0% | 0.0% | 0.0% |
| 6 | 16% | 12.0% | 0.0% | 0.0% |
| 7 | 20% | 15.0% | 0.0% | 0.0% |
| 8 | 17% | 15.0% | 3.0% | 0.0% |
| 9 | 13% | 15.0% | 0.0% | 0.0% |

TABLE 3-continued

Synergistic effect of ligninolytic bacteria on lignin degradation.

| Consortia No. | Percentage decolorization of lignin | | | |
|---|---|---|---|---|
| | 0.7% | 0.8% | 0.9% | 1.0% |
| 10 | 12% | 13.0% | 0.0% | 0.0% |
| 11 | 11% | 6.0% | 0.0% | 0.0% |
| 12 | 15% | 2.0% | 0.0% | 0.0% |
| 13 | 22% | 8.0% | 0.0% | 0.0% |
| 14 | 20% | 10.0% | 0.0% | 0.0% |
| 15 | 15% | 11.0% | 0.0% | 0.0% |
| 16 | 29% | 40% | 8.0% | 1.0% |
| 17 | 12% | 14.0% | 0.0% | 0.0% |
| 18 | 15% | 12.0% | 0.0% | 0.0% |
| 19 | 22% | 18.0% | 1.0% | 0.0% |
| 20 | 23% | 10.0% | 0.0% | 0.0% |

EXAMPLE 5

To find out the mechanism of lignin degradation at enzyme level, enzyme assay for lignin peroxidase, a key enzyme for lignin degradation, was carried out. All the three bacteria, L35, L36 and L13 of the consortium 16 (Table 3) which was able to degrade the lignin upto 0.8%, were inoculated individually in 1 liter minimal salt medium (MSM) having 1% glucose. For the induction of ligninolytic enzymes, 1 mM veratryl alcohol was added to the cultures. All the cultures were incubated at 30–35° C. for three days under shaking conditions (100–120 rpm). After seeing the heavy bacterial growth, all the cultures were centrifuged at 10,000 rpm at 4° C. Supernatant was collected to check the enzyme activity.

For the concentration of extracellular enzymes, 80% ammonium sulfate precipitation was carried out using 100% saturated ammonium sulfate solution followed by subsequent dialysis.

Enzyme assay for lignin peroxidase was performed for both, crude cell free extracts as well as concentrated sample. For the enzyme assay, 10 mM veratryl alcohol, 5 mM $H_2O_2$ and 400 µl enzyme solution was added in tartaric acid (pH 3) buffer. The formation of product (veratryldehyde) was monitored at 310 nm. Lignin peroxidase catalyzes the oxidation of veratryl alcohol by $H_2O_2$ to veratryldehyde. Veratry alcohol exhibits no absorbance at 310 nm whereas veratrlydehyde absorbs strongly (molar extinction coefficient=9300 M−1 cm−1). All the three bacterial isolates showed different degree of ligninolytic activity (table 4).

TABLE 4

Enzyme activity of L35, L36 and L13 in term of increase in O.D. after incubation of 15 minutes

| | | ABSORBANCE AT 310 nm | | | |
|---|---|---|---|---|---|
| | ISOLATE | 24 hrs. | | 72 hrs. | |
| S. NO. | NO. | INITIAL | FINAL | INITIAL | FINAL |
| 1 | L35 | 0 | 0 | 1.352 | 1.491 |
| 2 | L36 | 0 | 0 | 1.265 | 1.438 |
| 3 | L13 | 0 | 0 | 1.426 | 1.537 |

Advantages

1. Degradation of lignin by bacteria has tremendous significance for the bioremediation of pulp and paper industrial wastewater.
2. Bacterial degradation of lignin confers a new understanding of conversion of industrial lignin waste into useful commodities.

We claim:

1. A consortium of ligninolytic bacteria for degradation of lignin, said consortium comprising three bacterial strains having accession numbers MTCC 5094, MTCC 5095 and MTCC 5098, which are respectively *Serratia marcescens, Pseuodomonas aeruginosa* and *Pseuodomonas aeruginosa*.

2. The bacterial consortium as claimed in claim 1, wherein the three bacterial strains MTCC 5094, MTCC 5095 and MTCC 5098 are each present in the range of 20 to 40% by wt.

3. The bacterial consortium as claimed in claim 1, wherein the three bacterial strains MTCC 5094, MTCC 5095 and MTCC 5098 are each present in equal proportions.

4. The bacterial consortium as claimed in claim 1, wherein the bacteria are isolated from a mixture of sawdust and soil.

5. The bacterial consortium as claimed in claim 1, wherein the bacteria are isolated from a mixture of sawdust and soil from Roorkhee, Uttar Pradesh, India.

6. The bacterial consortium as claimed in claim 1, wherein the consortium exhibits lignin degradation of up to 0.8%.

* * * * *